United States Patent
Kieffer

(10) Patent No.: US 8,394,017 B2
(45) Date of Patent: Mar. 12, 2013

(54) BATTLEFIELD LARYNGOSCOPE ADAPTOR CAP FOR FLASHLIGHT

(76) Inventor: Lucan Miles Kieffer, Tigard, OR (US)

( * ) Notice: Subject to any disclaimer, the term of this patent is extended or adjusted under 35 U.S.C. 154(b) by 667 days.

(21) Appl. No.: 12/460,646

(22) Filed: Jul. 22, 2009

(65) Prior Publication Data

US 2010/0191062 A1    Jul. 29, 2010

Related U.S. Application Data

(60) Provisional application No. 61/146,840, filed on Jan. 23, 2009.

(51) Int. Cl.
*A61B 1/267* (2006.01)

(52) U.S. Cl. ........ 600/199; 600/185; 600/193; 600/246; 362/202; 362/293

(58) Field of Classification Search .................. 600/185, 600/190, 199, 181, 160, 178, 245, 248, 186, 600/188, 193, 194, 196, 197, 200, 246, 249; 128/200.26; 362/2, 293, 359, 885
See application file for complete search history.

(56) References Cited

U.S. PATENT DOCUMENTS

| | | | | |
|---|---|---|---|---|
| 3,638,644 A | * | 2/1972 | Reick | 600/191 |
| 5,014,723 A | * | 5/1991 | Kaufman | 128/853 |
| 5,471,374 A | * | 11/1995 | Palmer | 362/191 |
| 6,102,851 A | | 8/2000 | Mellin | |
| 6,454,704 B1 | * | 9/2002 | Dzwonkiewicz | 600/185 |
| 2003/0013937 A1 | * | 1/2003 | Tsujita et al. | 600/109 |
| 2007/0093693 A1 | * | 4/2007 | Geist et al. | 600/199 |
| 2010/0022843 A1 | * | 1/2010 | Pecherer et al. | 600/197 |

* cited by examiner

*Primary Examiner* — Kevin T Troung
*Assistant Examiner* — Samuel Hanna
(74) *Attorney, Agent, or Firm* — Mark S. Hubert

(57) ABSTRACT

A laryngoscope adaptor cap for use with existing government issue military flashlights designed for use in night time battlefield conditions. A filter disc filters out visible light and a light seal design prevents leakage of visible light from an assembled laryngoscope. The adaptor cap is crush resistant, impact resistant, has a high melting temperature, is disposable and allows the attachment of conventional laryngoscope paddles. It allows for night time endotracheal intubation in conjunction with military issue night vision goggles in the absence of visible light.

5 Claims, 6 Drawing Sheets

BATTLEFIELD LARYNGOSCOPE ADAPTOR CAP FOR FLASHLIGHT

This utility application claims the benefit of priority from provisional application 61/146,840 filed Jan. 23, 2009 and incorporates by reference all aspects of the provisional application.

BACKGROUND OF THE INVENTION

Currently there exists flashlight powered laryngoscopes as is detailed in U.S. Pat. No. 6,102,851 "Laryngoscopes with Removable Light Sources."

SUMMARY OF THE INVENTION

The general purpose of the present invention, which will be described subsequently in greater detail, is to provide an adaptor cap for a military flashlight that will eliminate the emission of all visible light and connect to conventional laryngoscope blades so as to enable a field medic to perform an endotracheal intubation procedure safely at night in battlefield conditions.

Similar, existing prior art devices utilize visible light, are not disposable, require the use of a non-military issue flashlight, do not have a light seal design, are not opaque, non-reflective, heat deformable, impact resistant, crush resistant and are physically large. Simply stated, they are not designed for use with existing government issue military equipment and are also not designed for use in night time battlefield conditions. When performing emergency medical procedures in night time battlefield conditions usually the injured patient cannot be moved and the medic is thus susceptible to hostile fire. Since endotracheal intubation with a laryngoscope requires a light source, such procedures marks the medic as a visible target.

The present invention has many of the advantages mentioned heretofore and many novel features that result in a new and novel battlefield laryngoscope adaptor cap for a flashlight which is not anticipated, rendered obvious, suggested, or even implied by any of the prior art, either alone or in any combination thereof.

In accordance with the invention, an object of the present invention is to provide a laryngoscope adaptor cap for a flashlight that eliminates all visible light emission.

It is a further objective of the present invention to provide a laryngoscope adaptor cap for a flashlight adapted with a light seal to eliminate unnecessary light leakage between the adaptor cap and the light source.

It is another objective of the present invention to provide a laryngoscope adaptor cap for a flashlight capable of impact resistance and resisting crushing forces as would be encountered in shifting weight in a military backpack.

It is still another objective of the present invention to provide a laryngoscope adaptor cap for a flashlight capable of inexpensive production so as to be disposable yet also capable of repeated sterilization.

It is a final objective of the present invention to provide a laryngoscope adaptor cap for a flashlight adapted for use with military issued night vision goggles.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

DETAILED DESCRIPTION

Figure 1:
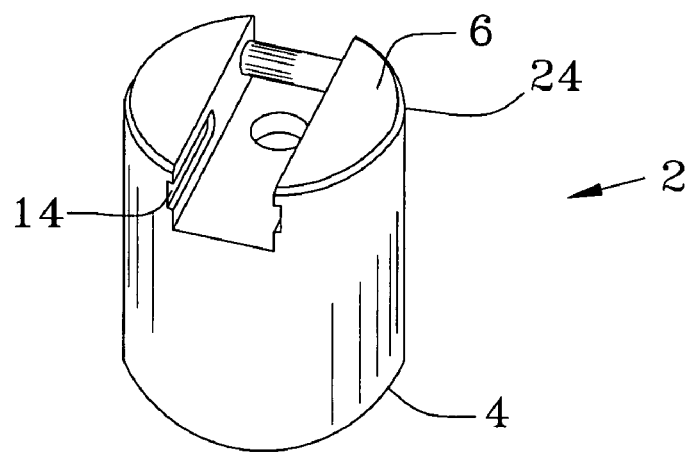
FIG. 1 is a top perspective view of the laryngoscope adaptor cap.
Figures 2, 3:
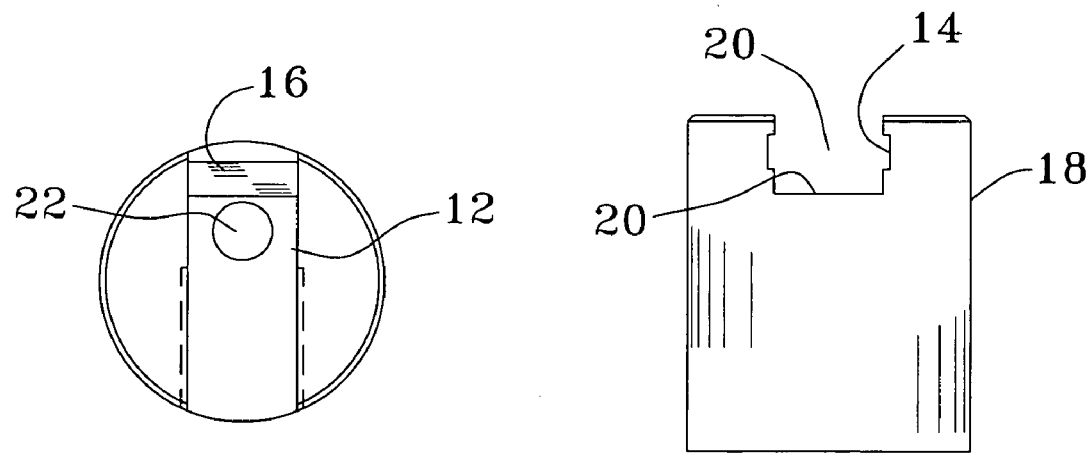
FIG. 2 is an end view of the laryngoscope adaptor cap.
FIG. 3 is a cross sectional side view of the laryngoscope adaptor cap.
Figure 4:
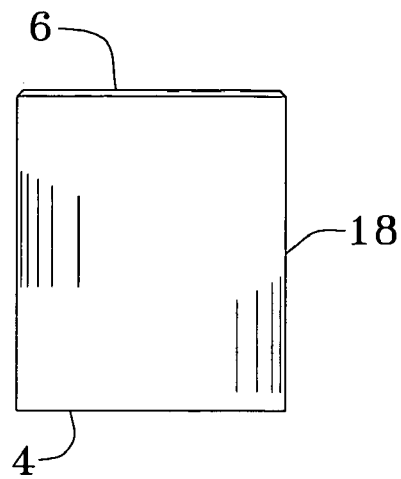
FIG. 4 is a side view of the laryngoscope adaptor cap rotated 90 degrees from FIG. 3.
Figure 5:
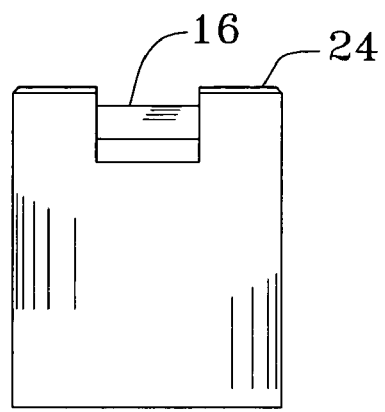
FIG. 5 is a side view of the laryngoscope adaptor cap rotated 90 degrees from FIG. 4.
Figure 8:
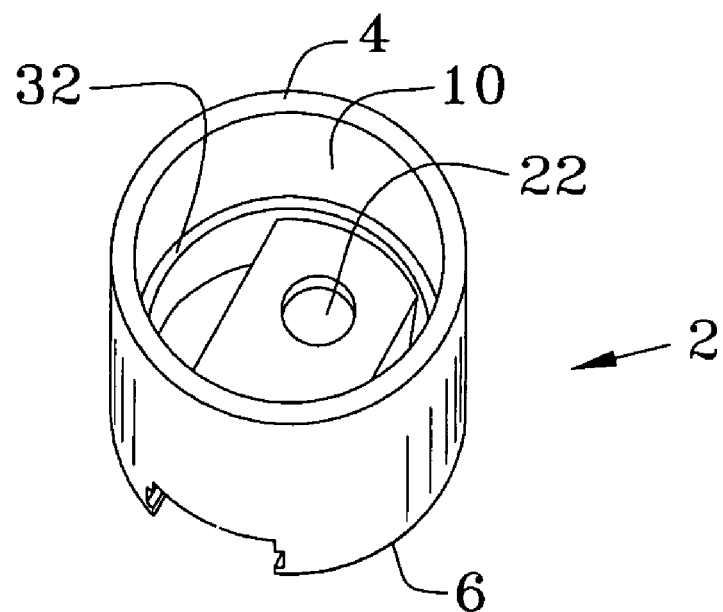
FIG. 8 is a bottom perspective view of the laryngoscope adaptor cap with the blackout filter disc removed.

Looking at FIGS. 1, 4 and 8 it can be seen that the adaptor cap 2 has a round, right cylindrical exterior configuration having an open lower distal end 4 adapted for receiving the bezel ring 28 of a flashlight 30 (FIG. 11), and an upper face 6 adapted for receiving a conventional laryngoscope blade 8 (FIG. 12) so as to form an internal cavity 10 therein. The upper face 6 has a rectangular dado 12 formed centrally thereon, having two parallel stopped grooves 14 (FIGS. 2 and 3). Each one of the grooves 14 are cut into one of the parallel side walls of the dado 12 beginning at the intersection of the dado 12 and the cylindrical side wall 18 of the adaptor cap 2. A cylindrical latching bar 16 extends between the side walls of the dado and resides parallel to the dado bottom face 20 although the longitudinal axes of the latching bar 16 and the dado bottom face 20 lie perpendicular to each other (FIG. 5). A cylindrical orifice 22 is formed through the dado bottom face 20 and into the internal cavity 10. The top peripheral edge of the upper face 6 has a slight chamfer 24 to reduce the possibility of lacerations due to the ability of the material of construction to hold an edge. This physical configuration matingly conforms to the connection section of a line of conventional laryngoscope blades known as green line fittings.

Figure 9:
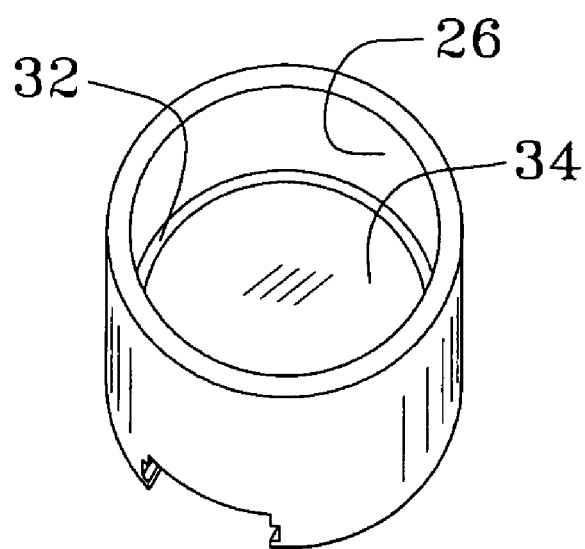
FIG. 9 is a bottom perspective view of the laryngoscope adaptor cap with the blackout filter disc installed.
Figure 10:
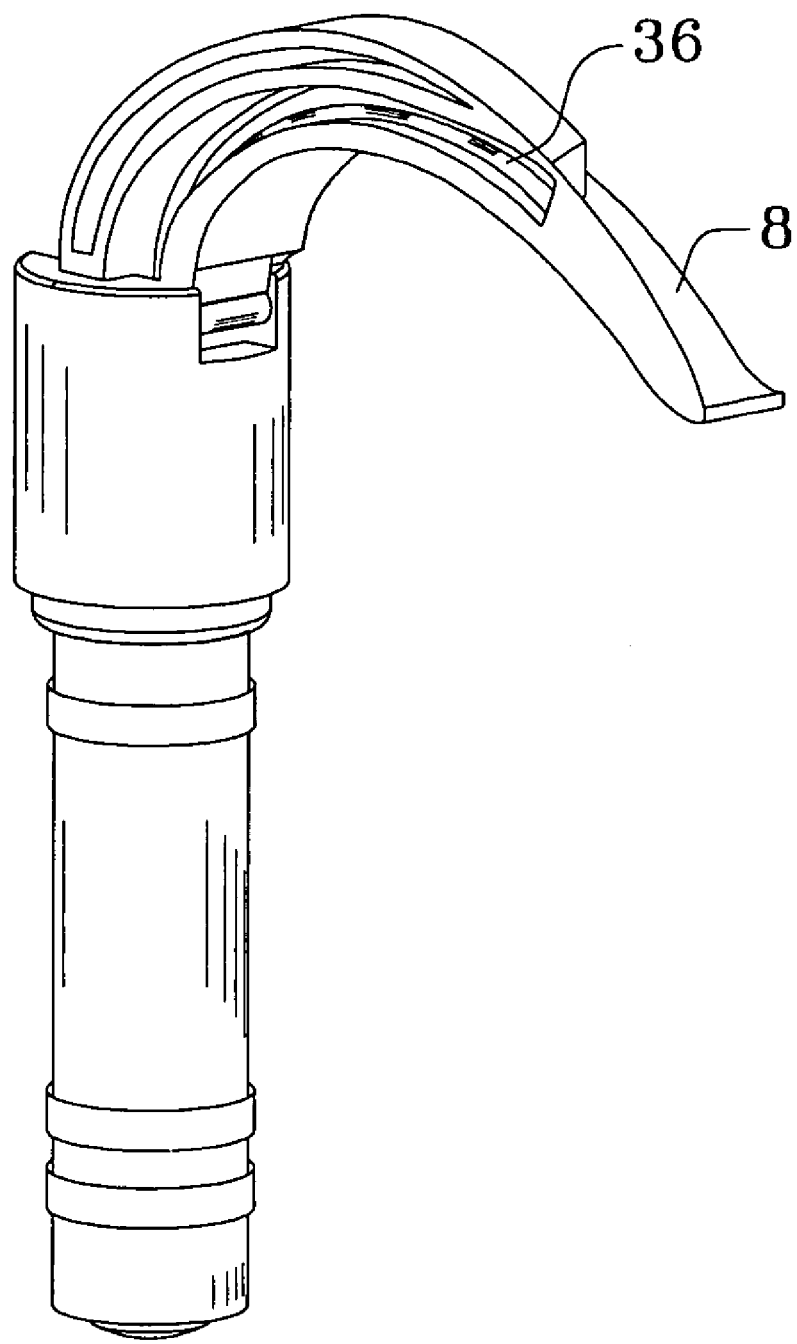
FIG. 10 is a perspective view of an assembled field laryngoscope utilizing the laryngoscope adaptor cap.
Figure 11:
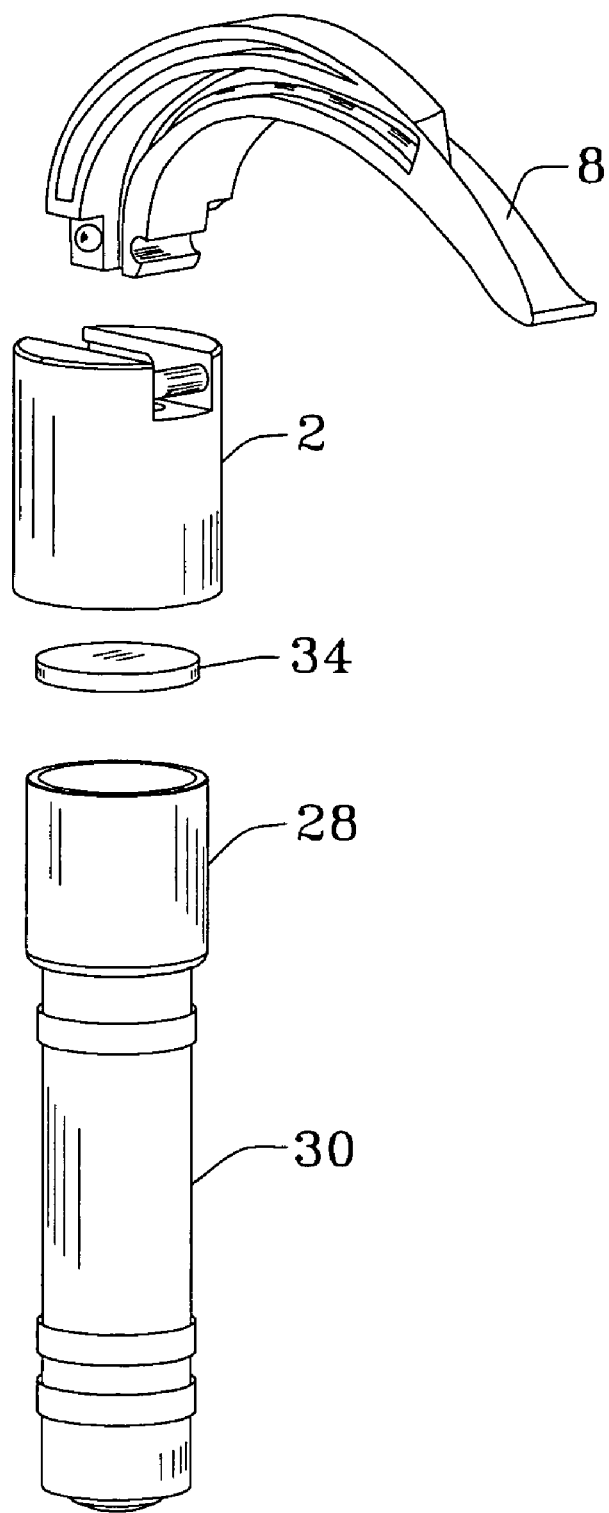
FIG. 11 is a perspective assembly view of an assembled field laryngoscope utilizing the laryngoscope adaptor cap.

Looking at FIGS. 8 and 9 it is best illustrated that the adapter cap internal wall 26 is extremely smooth and has a slight inward taper so as to form a light seal about the front bezel ring 28 of a flashlight 30 (FIG. 11). In the preferred embodiment this taper is one degree although a different taper may work better with a less hard material of construction or with flashlights that have a more resilient bezel ring. An inner circumferential flange 32 is formed on the adapter cap internal wall 26 and resides parallel to the edge of the lower distal end 4 and the upper face 6. Flange 32 has an outer diameter smaller than the diameter of the flashlight's bezel ring 28 yet larger than the diameter of the blackout filter disc 34, and an inner diameter that is smaller than the diameter of the blackout filter disc 34. In this way the blackout filter disc 34 can rest on the inner circumferential flange 32 yet not contact the bezel ring 28 of the flashlight 30. This design ensures that the blackout filter disc 34 resides deep enough into the internal cavity 10 that a 100% light seal is made between the bezel ring 28 and the adaptor cap internal wall 26 without the bezel ring 28 projecting deep enough into the internal cavity 10 to contact the blackout filter disc 34. The diameter of the opening in the lower distal end 4 is slightly greater than the diameter of the bezel ring 28 of the flashlight 30 it is designed to work with.

The adaptor cap 2 is made from an opaque, lightweight, electrically non-conductive, non-reflective, boilable, crush resistant, impact resistant, polymer. In the preferred embodiment it is made of a 50% glass-fibre reinforced engineering thermoplastic material based on a composition of semi-crystalline Polyamide with partially aromatic Copolyamide. Such a material has a high stiffness and strength, dimensional stability, low warpage, low water absorption, good chemical resistance, excellent impact resistance and will support a good surface finish. These are the material qualities that are needed in hot desert locations and under battlefield conditions to ensure that a proper light seal can always be made.

The preferred dimensions of the adaptor cap 2 are sized to accommodate a 1.25 inch diameter bezel ring 28. Military field flashlights such as the Surefire 6P, 9P, G2 and G3 are known to have this compatible dimension.

Figure 6:
FIG. 6 is a perspective view of the blackout filter disc.
Figure 7:
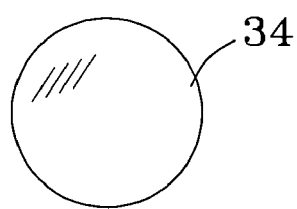
FIG. 7 is a front view of the blackout filter disc.

Looking at FIGS. 6 and 7 the blackout filter disc 34 can best be seen. It is a circular disc that restricts essentially 100% of the visible light (that light in the 380 nm to 750 nm wavelength range) emitted from an incandescent light source, and allows a select portion of infrared light (that light in the 750 nm to 100 μm wavelength range) to pass through. The disc 34 has a polysulfane base and is commonly referred to as an IR filter. In the preferred embodiment to work with standard government issue night vision goggles, a blackout filter disc 34 that allows a range of infrared light beginning at about a 850 nm wavelength to pass through, has been used. Such filter discs are well known in the industry and commercially available.

Although sterilizable, the adaptor cap 2 is designed to be disposable as it will be in contact with bodily fluids and comprise a biohazard problem after usage. The blackout filter disc 34 is the most expensive component and thus is designed to be reused with new adaptor caps 2.

Figure 12:
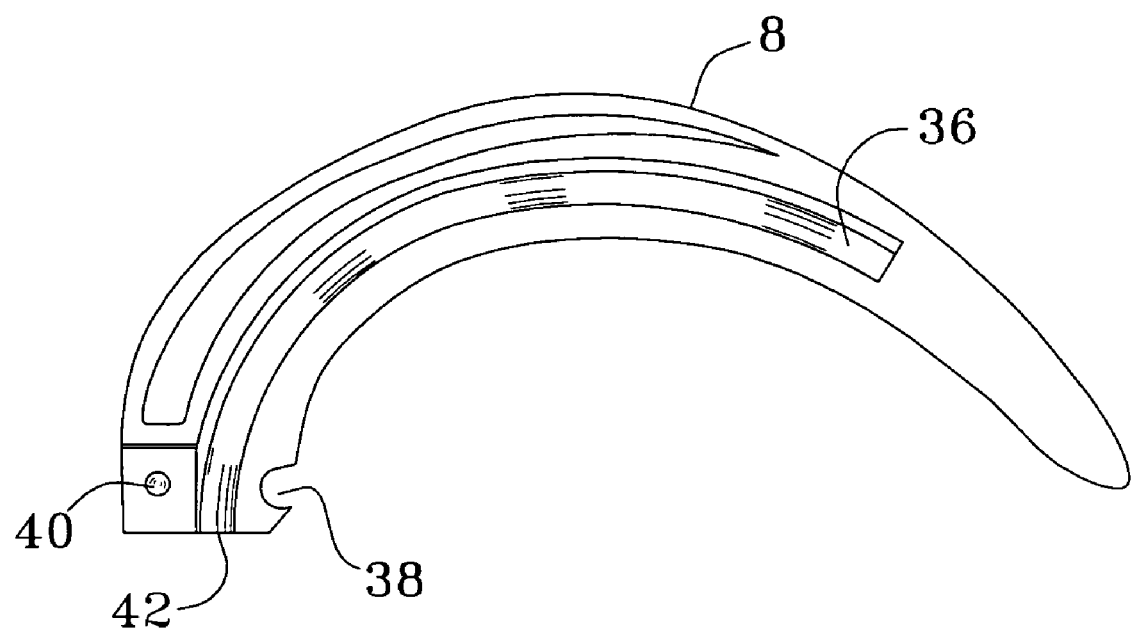
FIG. 12 is a side view of a conventional laryngoscope blade.

Looking at FIG. 12 a conventional laryngoscope blade 8 with a greenline fitting can be seen. Basically it is a curved planar blade with a fibre optic line 36 running along its length so as to align and focus the non-visible infrared light beam toward the blade tip and illuminate the patient's throat to anyone wearing a set of night vision goggles adapted for viewing infrared light in the 850 nm wavelength range and above. The attachment end of the blade 8 has a hook 38 that matingly engages the latching bar 16 and a set of two spring loaded detent balls 40 that matingly engage the two parallel stopped grooves 14 in the side walls of dado 12 on the adaptor cap 2. When the laryngoscope blade 8 is engaged onto the adaptor cap 2 the fibre optic line's trailing end 42 aligns with the adaptor cap orifice 22.

In operation, when the flashlight 30 is inserted into the adaptor cap 2 (with a blackout disc 34 seated on the flange 32) such that the flashlight bezel ring 28 is frictionally engaged about its perimiter with the tapered inner wall 26 so as to make a light seal, and when the light source (an incandescent flashlight) is switched on, only infrared light passes through the blackout filter disc 34, the orifice 22 and along the fibre optic line to the leading edge 44 of the laryngoscope blade 8. Anyone wearing the appropriate night vision goggles has a well illuminated view of the patient's throat as they perform an endothracheal intubation while to the rest of the world, no visible light is present. To get the frictionally tight light seal the flashlight 30 and adaptor cap 2 assembly must be brought together with a sharp physical rap.

It is to be noted that not all visible light emitting flashlights are suited for the above purpose. LED versions will not work with the blackout filter disk 34 in place. However, without the blackout filter disk 34 adaptor cap 2 is compatible with an LED flashlight. The preferred embodiment uses a flashlight with an incandescent light emitting bulb that produces visible "white" light or a fairly even distribution of all the visible spectrum appearing white to the eye. It was specifically designed to work in conjunction with the military issue Surefire Original™ 6P, 9P, G2 and G3 incandescent flashlights.

In the preferred embodiment the adaptor cap 2 is 1.25 inches long, 1.5 inches wide with a ⅜ inch deep dado 12 and a ⅛ inch diameter latching bar 16 centered ¼ of an inch off the top face 6. It is also to be noted that the grooves 14 cut into the parallel side walls of the dado 12 may be replaced by simple detents.

It is important to note the significance of the material of construction of the adaptor cap 2. The thermoplastic polymer product chosen is a Nylon 66™ base material with a 50% glass-fibre reinforcing fill (based on a composition of semi-crystalline Polyamide with partially aromatic copolyamide) having a product name of Grivory GV-5H™. Since the light seal is generally made by banging the flashlight into the adaptor cap against a hard surface, the material must be extremely impact resistant, and non-shattering (tensile strength is 18000 MPa dry as per ISO 527 standard and an impact strength of 80 kJ/m$^2$ dry as per ISO 179/1 eU). Because it is used in extreme heat conditions it must have a high melting point as any deformation would potentially compromise the light seal (melting temperature is 260 degrees F dry as per ISO 11357 standard).

Looking at FIG. 11 the disassembled field night vision laryngoscope can best be seen. The adaptor cap 2 is designed for use with the standard government issue flashlights and can be sized accordingly for any size of flashlight bezel ring. This allows the use of the adaptor cap 2 without the blackout filter disc 34. In this configuration without the blackout feature, a field laryngoscope can be made utilizing a government issue field flashlight (or any flashlight with a 1.25 inch diameter bezel ring) with the adaptor cap 2 and the blade 8.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention

Having thus described the invention, what is claimed as new and desired to be secured by Letters Patent is as follows:

1. A battlefield laryngoscope adaptor cap for making a light tight seal with a flashlight comprising:

an opaque, non reflective, impact resistant cylindrical cap configured for mating engagement with a laryngoscope blade, having a first open end at the most proximal end of the cap and an opposing second closed distal end with an orifice defined therethrough so as to form an internal cavity having a depth, said internal cavity having a smooth completely tapered interior wall that tapers smaller in diameter from said first proximal open end towards said second end and has an inner circumferential flange at said second distal end, said second end having an outer face with a dado formed centrally thereon, said dado having two parallel dado walls each with a stopped groove formed therein as a cut and having a cylindrical bar extending between said dado walls;

a visible light restricting filter disc;

wherein said filter disc resides upon said flange into the interior cavity of said cylindrical cap so that a 100% light seal is made between a flashlight bezel ring and said adaptor cap interior wall without the bezel ring contacting the light restricting filter disc, and allows only infrared light to pass from said cavity through said orifice said cap has a melting point that exceeds 212 degrees Fahrenheit, said smooth completely tapered interior wall has a 1 degree taper and said cap is made of a 50% glass-fiber reinforced engineering thermoplastic material based on a composition of semi-crystalline Polyamide with a particularly aromatic Copolyamide such that the cap is extremely impact resistant, and non-shattering, having a tensile strength that is 18000 MPa dry as per ISO 527 standard and an impact strength of 80 kJ/m$^2$ dry as per ISO 179/1 eU, such that when said flashlight is mated to said cap by banging the flashlight into the adaptor cap against a hard surface, the adapter cap does not shatter and said completely tapered inner wall forms a light tight-seal with a bezel ring of said flashlight when inserted into said cavity.

2. The battlefield laryngoscope adaptor cap of claim 1 wherein said cap is fabricated from a crush resistant polymer.

3. The battlefield laryngoscope adaptor cap of claim 1 wherein said filter allows the passage of infrared light having a wavelength greater than 850 nm.

4. The battlefield laryngoscope adaptor cap of claim 3 wherein said bezel ring measures approximately 1.25 inches in diameter.

5. The battlefield laryngoscope adaptor cap of claim 1 wherein said cap has an overall length from second end to said first open end of approximately 1.625 inches.

* * * * *